United States Patent [19]

Uyeda

[11] 4,008,331

[45] Feb. 15, 1977

[54] ANTIDEPRESSANT 1,1a,6,10b-TETRAHYDRODIBENZO-[a,e]-CYCLOPROPA-[c]-CYCLOHEPTEN-6-SUBSTITUTED OXIMES

[75] Inventor: Roy Teruyuki Uyeda, Newark, Del.

[73] Assignee: E. I. Du Pont de Nemours and Company, Wilmington, Del.

[22] Filed: Mar. 15, 1976

[21] Appl. No.: 667,274

Related U.S. Application Data

[60] Division of Ser. No. 616,483, Sept. 26, 1975, Pat. No. 3,960,956, which is a continuation-in-part of Ser. No. 525,877, Nov. 21, 1974, abandoned.

[52] U.S. Cl. .............................................. 424/327
[51] Int. Cl.² .................................... A61K 31/155
[58] Field of Search .................................. 424/327

Primary Examiner—Stanley J. Friedman

[57] ABSTRACT

Antidepressant 1,1a,6,10b-tetrahydrodibenzo-[a,e]-cyclopropa-[c]-cyclohepten-6-substituted oximes and their pharmaceutically suitable salts useful for alleviating depression in mammals.

12 Claims, No Drawings

ANTIDEPRESSANT 1,1a,6,10b-TETRAHYDRODIBENZO-[a,e]-CYCLOPROPA-[c]-CYCLOHEPTEN-6-SUBSTITUTED OXIMES

CROSS-REFERENCE TO RELATED APPLICATION

This is a division of application Ser. No. 616,483, filed Sept. 26, 1975, now U.S. Pat. No. 3,960,956 which application is a continuation-in-part of my co-pending application Ser. No. 525,877, filed Nov. 21, 1974, now abandoned.

BACKGROUND

This invention relates to tetracyclic antidepressants, dibenzocycloheptenes with a nuclearly fused cyclopropyl moiety.

Dostert and Kyburz (U.S. Pat. No. 3,803,234) disclose N-(aminoalkyl or heterocyclic aminoalkyl) dibenzocycloheptene imine derivatives.

Judd (U.S. Pat. No. 3,349,128) discloses dibenzocycloheptenes having an aminoalkylene ether attached to the imino nitrogen but without the nuclear fused cyclopropyl moiety.

The following patents relate to compounds with the same basic carbon skeleton but different substituents in the 6-position: Coyne (U.S. Pat. No. 3,574,199), aminoalkyl or aminoalkylidene; Coyne (U.S. Pat. No. 3,547,933 and U.S. Pat. No. 3,658,908), hydroxy or lower alkanoyloxy and various aminoalkyl groups; Remy (U.S. Pat. No. 3,475,438), N-alkyl piperidine; Uyeda (Belgian Pat. No. 805,433 and French Pat. No. 2,201,089), alkylated imine.

Mental illness encompasses both psychoses and neuroses. Symptoms requiring treatment include depression, anxiety, agitation, and hallucinations. Among the drugs used particularly for treatment of both reactive and endogenous depressions are monoamine oxidase (MAO) inhibitors, such as iproniazide, tranylcypromine, nialamide, phenelzine, and pargyline, and the non-MAO-inhibiting tricyclic aromatic dibenzazepines, such as imipramine, and dibenzocycloheptenes such as amitriptyline.

All of these drugs have adverse side effects that limit their usefulness. MAO inhibitors may benefit milder forms of depression, but the risk of serious toxic effects is a strong argument against their use. They may cause liver damage and acute hypertension, especially if given in conjunction with cheese, bananas, or other amine-containing foods. The MAO inhibitors may also cause tremors, insomnia, hyperhydrosis, agitation, hypermanic behavior, confusion, hallucinations, convulsions and orthostatic hypotension. They frequently cause dizziness, vertigo, headache, inhibition of ejaculation, difficulty in urination, weakness, fatigue, dry mouth, constipation and blurred vision.

Imipramine may cause blurred vision, dryness of mouth, constipation, urinary retention, orthostatic hypotension, respiration depression, myocardial infarction, and congestive heart failure. Similar difficulties are experienced with amitriptyline.

There is a continuing need for psychotherapeutic agents that have fewer side effects than the drugs in use today; also for psychotherapeutic agents that have different modes of action than presently used agents, since none of these is completely effective.

The present invention results from efforts to develop new, safe, and effective psychotherapeutic compounds with minimal side effects.

SUMMARY

According to this invention there is provided novel compounds of formula I and their pharmaceutically suitable salts, processes for their manufacture, compositions containing them, and methods of using them to alleviate depression in mammals.

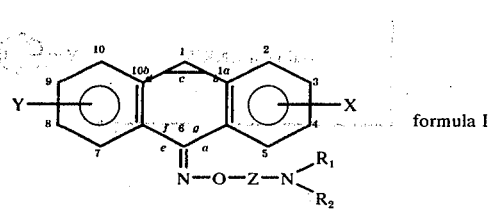

formula I where
X or Y = H, F, Cl, Br, $C_1$–$C_4$ alkyl, $C_1$–$C_4$ alkoxy, $CF_3$, $CH_3S$, $CH_3SO_2$, $SO_2N(CH_3)_2$, provided that one is H;
Z = $C_2$–$C_3$ alkylene;
$R_1$ and $R_2$ independently = H, $C_1$–$C_4$ alkyl, or together can form a ring with N;

in which W can be
—$(CH_2)_4$—, —$(CH_2)$ or
—$(CH_2)_2O(CH_2)_2$—.

DETAILED DESCRIPTION

Preferred Compounds

Compounds preferred because of their high degree of activity are those in which $R_1$ and $R_2$ = H or $CH_3$.

More preferred are those in which X and Y = H, Z = ethylene, and $R_1$ and $R_2$ = H or $CH_3$.

The compound most preferred is that in which X and Y = H, Z = ethylene, and $R_1$ and $R_2$ = H.

Pharmaceutical Salts

Pharmaceutically suitable acid addition salts of these compounds include those made with physiologically acceptable acids that are known in the art; such salts include hydrochloride, sulfate, nitrate, phosphate, citrate, tartrate, maleate and the like.

Synthesis

Compounds of this invention are prepared as shown in the following general reaction scheme.

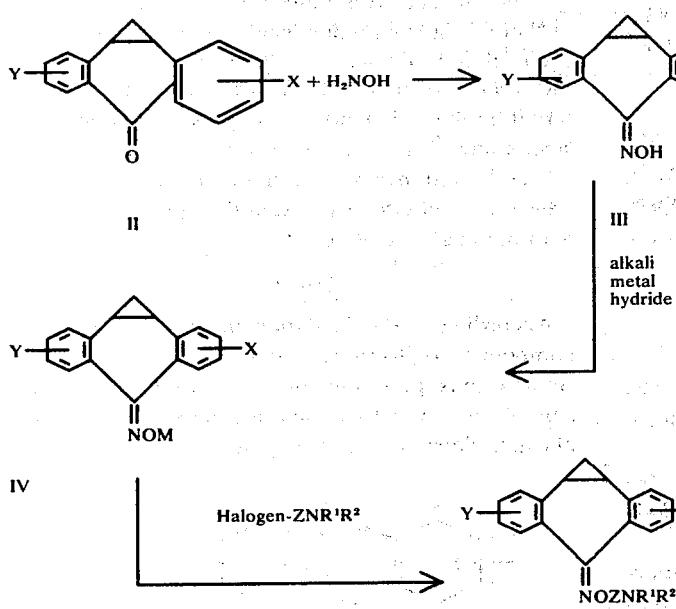

in which $R^1$, $R^2$, X, Y and Z are as previously defined and M is an alkali metal.

Another method of preparing some of the compounds involves reaction of the oxime of a dibenzocyclopropacycloheptene in the form of its alkali metal salt, e.g., sodium, with ethylene oxide to give the corresponding O-β-hydroxyethyloxime, which is converted to its tosylate by reaction with p-toluenesulfonylchloride. The tosylate reacts with a hydrogen bearing amine to give the aminoalkyloximes as shown by the following

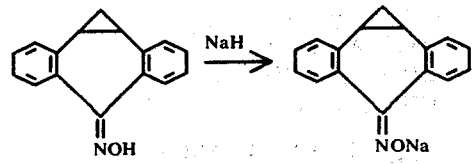

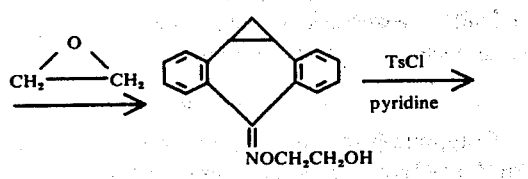

-continued

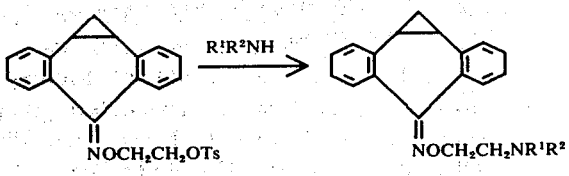

Another method for preparation of the O-β-hydroxyethyloxime of dibenzocyclopropacycloheptene is the treatment of 1,1a,6,10b-tetrahydrodibenzo[a,e]cyclopropa[c]cyclohepten-6-one dimethylketal with carboxymethoxylamine hemihydrochloride to give the O-α-carboxymethyloxime derivative. Reduction of this acid with borane-THF complex or borane dimethylsulfide complex gives the O-β-hydroxyethyloxime as shown by the following:

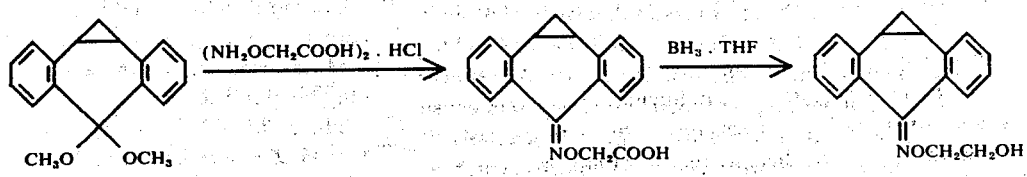

The nuclearly substituted 1,1-dichloro-1,1a,6,10b-tetrahydrodibenzo[a,e]cyclopropa[c]cyclohepten-6-ones used as precursors can be prepared by treating 5H-dibenzo[a,d]-cyclohepten-5-ones under anhydrous conditions with sodium methoxide and ethyltrichloroacetate or heating at reflux a benzene solution of the ketone and phenyltrichloromethyl mercury to form 1,1-dichloro-1,1a-6,10-b-tetrahydrodibenzo[a,e]cyclopropa[c]cyclohepten-6-ones of the general formula:

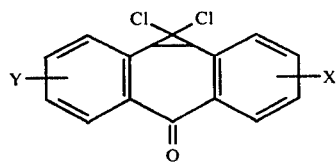

and subsequently reducing the dichloroketone to the corresponding carbinol by treatment in solution with sodium borohydride to produce the alcohol. The gem chlorines and any halogen on the benzene rings can be replaced with hydrogen by treatments of the dichloroalcohol with lithium and tert.-butanol followed by oxidation with chromium trioxide in sulfuric acid or chromium trioxide in pyridine to form the precursors (II).

The basic starting material, 5H-dibenzo[a,d]cyclohepten-5-one is commercially available. Synthesis of the benzo-substituted analogs can be carried out by adaptation of the synthesis procedures shown in:

A.C. Cope et al., J. Am. Chem. Soc. 73, 1673 (1951)
W. Treibs et al., Ber. 84, 671 (1951)
S. O. Winthrop et al., J. Org. Chem. 27, 230 (1962).

Another method of preparing the precursor compounds is addition of dichlorocarbene to the commercially available 5H-dibenzo[a,d]cyclohepten-5one by the method described in U.S. Pat. No. 3,547,933 to give 1,1-dichloro-1,1a,6,-10b-tetrahydrodibenzo[a,e]-cyclopropa[c]cyclophepten-6-one. Treatment of this dichloroketone with POCl₃-PCl₅ followed by sodium methoxide in methanol or triethylamine in methanol gives 1,1-dichloro-1,1a,6,10b-tetrahydrodibenzo[a,e]-cyclopropa[c]cyclohepten-6-one dimethylketal. Both chlorine atoms can be replaced with hydrogen by reaction with lithium hydride-triethylborane (lithium triethylborohydride) in hexamethylphosphoramide to give 1,1a,6,10b-tetrahydrodibenzo[a,e]cyclopropa[c]cyclohepten-6-one-dimethylketal. Treatment of this ketal with acid yields 1,1a,6,10b-tetrahydrodibenzo[a,e]cyclopropa[c]cyclohepten-6-one. Reaction of this ketone with hydroxylamine gives the 1,1a,6,10b-tetrahydrodibenzo[a,e]cyclopropa[c]cyclohepten-6-one oxime. An advantage of this synthesis is retention of substituents, such as halogen, on one or more of the benzene rings.

Another method of preparing the precursor compounds is by treating the respective 5-H-dibenzo[a,d]cyclohepten-5-ones with bromoform and base[1] or heating at reflux a benzene solution of the ketone and phenyltribromomethyl mercury to form the respective 1,1-dibromo-1,1a,6,10b-tetrahydrodibenzo[a,e]cyclopropa[c]cyclohepten-6-ones of the general formula:

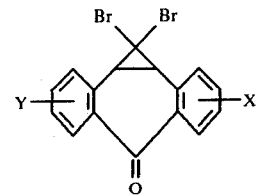

Treatment of this dibromoketone with POCl₃-PCl₅ followed by triethylamine in methanol gives 1,1-dibromo-1,1a,6,10b-tetrahydrodibenzo[a,e]cyclopropa[c]cyclohepten-6-one dimethylketal. Replacement of both of the bromine atoms with hydrogen is effected by reflux with lithium aluminum hydride in tetrahydrofuran, or lithium in tert-butanol, or lithium hydride-triethylbroane (lithium triethylborohydride) in hexamethylphosphoramide to give 1,1a,6,10b-tetrahydrodibenzo[a,e]cyclopropa[c]cyclohepten-6-one dimethylketal. Treatment of this ketal with hydroxylamine hydrochloride in pyridine gives the 1,1a,6,10b-tetrahydrodibenzo[a,e]cyclopropa[c]cyclohepten-6-one oxime.

1. 1,1-Dibromodibenzocyclopropacycloheptenone (A, X=Y=H) was first reported by S. Winstein and R. F. Childs, J. Am. Chem. Soc., 89, 6348 (1967).

The oxime is readily formed by treatment of the 6-oxo compound with hydroxylamine, generally at 50°–125° for 10–24 hours. in the presence of a tertiary amine such as pyridine as illustrated by Example 1A below.

Another method of preparing the precursor 1,1a,6,10b-tetrahydrodibenzo[a,e]cyclopropa[c]cyclohepten-6-one oxime is by the reaction of 1,1a,6,10b-tetrahydrodibenzo[a,e]cyclopropa[c]cyclohepten-6-one dimethylketal with hydroxylamine hydrochloride in pyridine as illustrated by Example 1c.

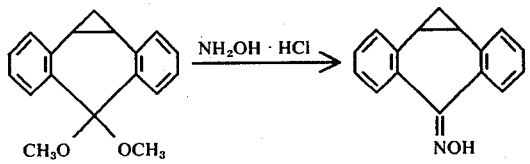

Substituted oximes are prepared from the oxime by formation of an alkali metal salt, suitably by reaction with a molar amount of an alkali metal hydride, such as readily available sodium hydride. The alkali metal salt is then reacted with a halide, Hal—ZNR¹R², in an inert, anhydrous solvent, such as hexamethylphosphoramide, generally at 10°–50° for a few minutes to an hour or more. The inorganic alkali metal halide is removed by washing, and the O-substituted oxime separated and purified.

The O-substituted oximes can also be prepared by treating the ketone II or its dimethylketal derivative with the appropriately O-substituted hydroxylamine hydrochlorides in pyridine as shown:

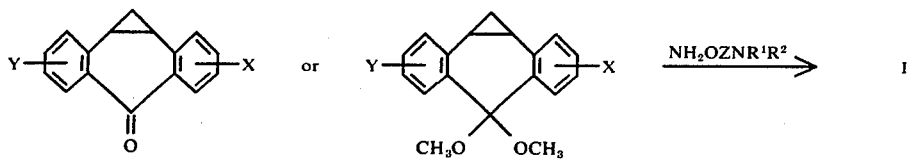

The compounds of this invention have a basic group, i.e., an amino or substituted amino group, that is 2–4 carbons removed from the oxygen ether linkage. This amino group is salt forming and facilitates the preparation of aqueous solutions for pharmaceutical use.

In addition, unlike the corresponding imines, these compounds have superior stability under hydrolytic conditions. For example, a solution of 0.6 g of N-(2-methylaminoethyl)-1,1a,6,10b-tetrahydrodibenzo[a,e]cyclopropa[c]cyclohepten-6-imine in 20 ml of 0.5M hydrochloric acid was stirred at 25° for 20 hrs. The solution was cooled and 10 ml of 10% sodium hydroxide solution was added, and the oil was twice extracted with a solution of 25% methylene chloride in ether. The combined organic extracts were thoroughly washed with saturated brine, dried and solvent removed. The NMR spectrum of the residue (0.5 g) indicated about 40% decomposition of the imine to the ketone occurred.

Following the same procedure 1,1a,6,10b-tetrahydrodibenzo[a,e]cyclopropa[c]cyclohepten-6-one O-[2-(methylamino)ethyl]oxime showed no detectable decomposition. This stability to hydrolysis is advantageous in preparation, storage, and use of pharmaceutical dosage forms.

In the following illustrative examples all parts are by weight and temperatures are centigrade unless stated to be otherwise.

EXAMPLE 1

A.

1,1a,6,10b-Tetrahydrodibenzo[a,e]cyclopropa[c]cyclohepten-6-one Oxime

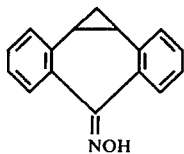

A solution of 6.6 g (0.03 mole) of 1,1a,6,10b-tetrahydrodibenzo[a,e]cyclopropa[c]cyclohepten-6-one, 8.4 g (0.12 mole) of hydroxylamine hydrochloride in 120 ml of pyridine was held at reflux for 18.5 hrs. The solvent was evaporated under reduced pressure and the residue was dissolved with a mixture of water and methylene chloride. The layers were separated and the organic layer was in turn washed with 10% hydrochloric acid, and saturated brine, dried and solvent evaporated to give 7.4 g of crude 1,a,6,10b-tetrahydrodibenzo[a,e]cyclopropa[c]cyclohepten-6-one oxime, mp 201° (ex. MeOH, dried at 110°/0.1 mm). The NMR spectrum in CDCl₃-DMSO-d₆: a singlet at δ10.9 (1H), multiplet at 6.9–7.6 (8H), multiplet at 2.1–2.6 (2H) and multiplet at 1.3–1.8 (2H). Anal. Calcd. for C₁₆H₁₃NO: C, 81.46; H, 5.57; N, 5.95. Found: C, 81.48; H, 5.68; N, 6.08. Mass spec.: Calcd. for C₁₆H₁₃NO: 235.0996. Found: 235.0997.

B.

1,1a,6,10b-Tetrahydrodibenzo[a,e]cyclopropa[c]cyclohepten-6-one O-[2-(dimethylamino)ethyl]oxime

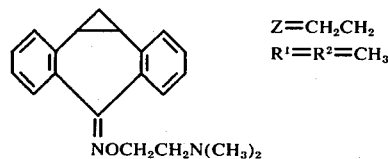

A dispersion of 2.5 g of 50% sodium hydride in mineral oil (0.052 mole of NaH) was thoroughly washed with hexane. To the sodium hydride, a solution of 4.8 g (0,020 mole) of 1,1a,6,10b-tetrahydrodibenzo[a,e]cyclopropa[c]cyclohepten-6-one oxime in 80 ml of anhydrous hexamethylphosphoramide (HMPA) was added and the mixture was stirred at 25° for 1 hr under nitrogen. To the oxime salt thus formed was added 3.8 g (0.026 mole) of anhydrous 2-dimethylaminoethylchloride hydrochloride and the mixture was stirred at 25° for 72 hrs. The reaction was quenched by the careful addition of 40 ml of water, then the mixture was poured into excess water. The oil was extracted twice with ether and the combined organic layers were extracted twice with 50 ml of 10% hydrochloric acid. The acidic solution was thoroughly washed with ether, then treated with an excess of sodium hydroxide solution. The oil was extracted with ether, washed with saturated brine, dried and solvent removed. The residue was titurated with hexane to give 3.8 g of 1,1a,6,10b-tetrahydrodibenzo[a,e]cyclopropa[c]cyclohepten-6-one O-[2-(dimethylamino)ethyl]oxime, mp 69°–70° (from cyclohexane). The MNR spectrum (CDCl₃): multiplet at δ6.9–7.5 (8H), triplet (J=6Hz) at 4.3 (2H), singlet at 2.2 superimposed on a multiplet at 2.2–3.9 (10H) and a multiplet at 1.3–1.9 (2H). Anal. Calcd. for C₂₀H₂₂N₂O: C, 78.40; H, 7.24; N, 9.14. Found: C,78.50; H, 7.01; N, 8,96 Mass spec.: Calcd. for C₂₀H₂₂N₂O: 306.1731, Found: 306.1694.

C.

1,1a,6,10b-Tetrahydrodibenzo[a,e]cyclopropa[c]cyclohepten-6-one Oxime

A solution of 1.5 g (5.6 moles) of 1,1a,6,10b-tetrahydrodibenzo[a,e]cyclopropa[c]cyclohepten-6-one dimethylketal, 2.5 g of hydroxylamine hydrochloride in 20 ml of pyridine was held at reflux for 18 hr. The solvent was removed under reduced pressure and the residue was dissolved with a mixture of water and methylene chloride. The layers were separated and the organic layer was in turn washed with 10% hydrochloric acid, saturated sodium bicarbonate solution and saturated brine, dried and solvent removed to give 1,1a,6,10b-tetrahydrodibenzo[a,e]cyclopropa[c]cyclohepten-6-one oxime. All of the physical properties were identical to those obtained by Example 1A. Note: The oxime forms a solvate with methanol.

EXAMPLE 2

1,1a,6,10b-Tetrahydrodibenzo[a,e]cyclopropa[c]cyclohepten-6-one 0-[2-(dimethylamino)ethyl]oxime hydrochloride

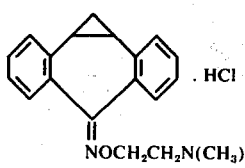

1,1a,6,10b-Tetrahydrodibenzo[a,e]cyclopropa[c]cyclohepten-6-one 0-[2-(dimethylamino)ethyl]oxime prepared as in Example 1 was dissolved in ether and saturated with anhydrous hydrogen chloride. The precipitate was filtered and thoroughly washed with ether. The product was recrystallized from acetonitrile, and dried at 100° (0.1 mm), mp 169°–171°.

EXAMPLE 3

1,1a,6,10b-Tetrahydrodibenzo[a,e]cyclopropa[c]cyclohepten-6-one 0-[2-(methylamino)ethyl]oxime

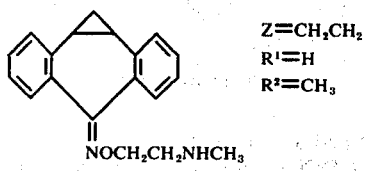

A dispersion of 1.5 g of 40% sodium hydride in mineral oil (0.025 mole of NaH) was thoroughly washed with hexane. To the sodium hydride, a solution of 2.4 g (0.010 mole) of 1,1a,6,10b-tetrahydrodibenzo[a,e]cyclopropa[c]cyclohepten-6-one oxime in 40 ml of dry hexamethylphosphoramide (HMPA) was added. The mixture was stirred at 25° for 1 hr under nitrogen. To the oxime salt was added 1.7 g (0.012 mole) of 2-methylaminoethylchloride hydrochloride and the mixture was stirred at 25° for 16 hrs. The reaction was processes as in Example 1 to give 25 g of an oil. Chromatography on 25 g of silica gel with ether as the eluent removed unreacted starting oxime. The crude product was obtained with methanol-1% triethylamine as eluent. Flash distillation (0.1μ, 180° bath) of the methanol fractions gave 1,1a,6,10b-tetrahydrodibenzo[a,e]cyclopropa[c]cyclohepten-6-one 0-[2-(methylamino)ethyl]oxime, MP 100°–101° C. NMR spectrum (CDCl$_3$): multiplet at δ6.8–7.5 (8H), triplet (J=6 Hz) at 4.2 (2H), tirplet (J=6 Hz) at 2.8 (2H), singlet at 2.4 superimposed on a multiplet at 2.1–2.5 (5H) and a multiplet at 1.3–1.8 (3H). Mass. spec: Calcd. for C$_{19}$H$_{20}$N$_2$O: 292.1575; Found: 292.1546.

In Examples 4–11 reaction of 1,1a,6,10b-tetrahydrodibenzo[a,e]cyclopropa[c]cyclohepten-6-one oxime as its sodium salt with the recited alkylhalide as described in Example 1 gives the indicated product.

EXAMPLE 4

1,1a,6,10b-Tetrahydrodibenzo[a,e]cyclopropa[c]cyclohepten-6-one 0-[3-(dimethylamino)propyl]oxime

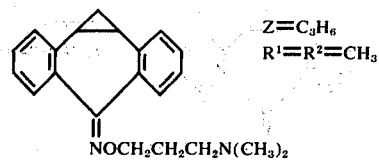

This compound was prepared by the process of Example 1 using 3-dimethylaminopropylchloride hydrochloride as the halogen amino compound. Crystals obtained from its solution in cyclohexane showed a melting point of 83°–83.5°.

NMR spectrum (CDCl$_3$): multiplet at δ7.0–7.5 (8H), triplet (J=6 Hz) at 4.2 (2H), singlet at 2.1 superimposed on a multiplet at 2.1–2.7 (10H) and multiplet at 1.3–2.1 (4H). Anal. Calcd. for C$_{21}$H$_{24}$N$_2$O: C, 78.71; H, 7.55; N, 8.74. Found: C, 78.79; H, 7.42; N, 8.73. Mass Spec: Calcd. for C$_{21}$H$_{25}$N$_2$O (M+1): 321.1995. Found: 321.2009.

EXAMPLE 5

1,1a,6,10b-Tetrahydrodibenzo[a,e]cyclopropa[c]cyclohepten-6-one 0-[2-(morpholino)ethyl]oxime

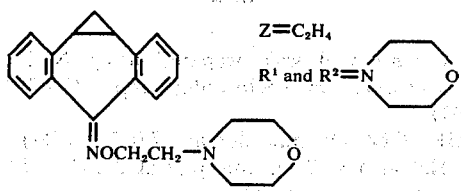

This compound was prepared by the process of Example 1 using N-(2-clorethyl)morpholine hydrochloride. Melting point 90°–91°, crystallized from isopropyl alcohol.

NMR (CDCl$_3$): multiplet at δ7.0–7.6 (8H), triplet (J=6 Hz) at 4.3 (2H), multiplet at 3.5–3.9 (4H), multiplet at 2.2–2.8 (8H) and multiplet at 1.4–1.8 (2H).

EXAMPLE 6

1,1a,6,10b-Tetrahydrodibenzo[a,e]cyclopropa[c]cyclohepten-6-one 0-[2-(pyrrolidino)ethyl]oxime

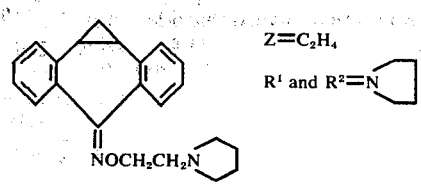

This compound was prepared using N-(2-chloroethyl)pyrrolidine hydrochloride. M.P. (ex. i-propyl alcohol) 96°–96.5°.

NMR (CDCl$_3$): multiplet at δ7.0–7.7 (8H), triplet (j=6 Hz) at 4.3 (2H), multiplet at 2.1–3.0 (8H) and multiplet at 1.4–1.9 (6H).

EXAMPLE 7

1,1a,6,10b-Tetrahydrodibenzo[a,e]cyclopropa[c]cyclohepten-6-one O-(2-aminoethyl)oxime

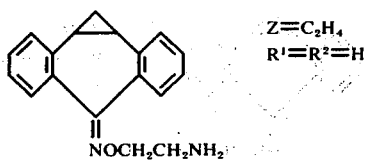

This compound was prepared using 2-chlorethylamine hydrochloride; mp 133°–134° (ex iPrOH).

NMR (CDCl$_3$): multiplet at δ7.0–7.5 (8H), triplet (J=6 Hz) at 4.2 (2H), triplet (J=6 Hz) at 2.9 (2H), multiplet at 2.2–2.6(2H), multiplet at 1.4–1.9 (2H) and singlet at 1.2 (2H, exchangeable with D$_2$O).

EXAMPLE 8

1,1a,6,10b-Tetrahydrodibenzo[a,e]cyclopropa[c]cyclohepten-6-one O-(2-piperidinoethyl)oxime

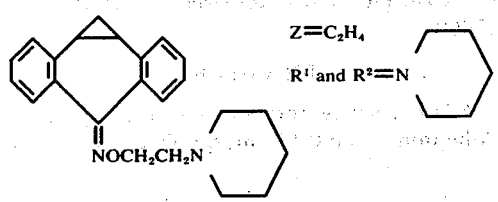

This compound was prepared using N-(2-cloroethyl)piperidine hydrochloride; mp 75°–76° (ex. iPrOH).

NMR (CDCl$_3$): multiplet at δ7.0–7.6 (8H), triplet (J=6 Hz) at 4.3 (2H), multiplet at 2.2–2.9 (8H) and multiplet at 1.3–1.8 (8H).

EXAMPLE 9

1,1a,6,10b-Tetrahydrodibenzo[a,e]cyclopropa[c]cyclohepten-6-one O-[2-(diisopropylamino)ethyl]oxime

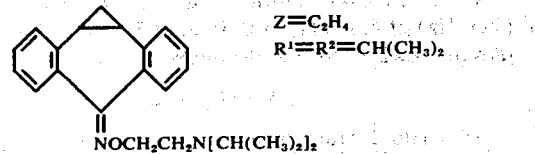

This compound was prepared using 2-diisopropylaminoethyl hydrochloride; mp 97°–98° (ex. iPrOH):

NMR (CDCl$_3$): multiplet at δ7.0–7.6 (8H), triplet (J=7 Hz) at 4.1 (2H), multiplet at 2.2–3.2 (6H), multiplet at 1.4–2.0 (2H) and doublet (J=7 Hz) at 1.0 (12H).

EXAMPLE 10

1,1a,6,10b-Tetrahydrodibenzo[a,e]cyclopropa[c]cyclohepten-6-one O-[3-(piperidino)propyl]oxime.

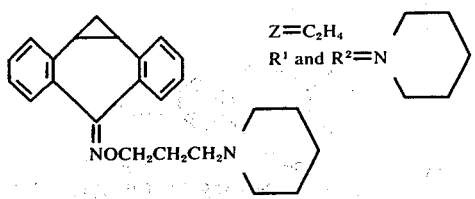

This compound was prepared using N-(3-chloropropyl) piperidine hydrochloride. It was flash distilled at 2μ (200° bath). NMR (CDCl$_3$): multiplet at δ6.9–7.5 (8H), triplet (j=6 Hz) at 4.2 (2H), and multiplet at 1.1–2.7 (18H).

EXAMPLE 11

1,1a,6,10b-Tetrahydrodibenzo[a,e]cyclopropa[c]cyclohepten-6-one O-[2-(dimethylamino)ethyl]oxime

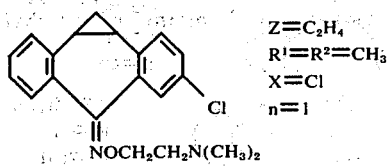

Flash distilled at 0.1μ (160° bath).

NMR (CDCl$_3$): multiplet at δ7.0–7.5 (7H), triplet (J=6 Hz) at 4.3 (2H), singlet at 2.2 superimposed on a multiplet at 2.1–2.9 (10H) and multiplet at 1.4–1.8 (2H).

The 4-clorodibenzocycloheptenone oxime was obtained by reaction of 4-chloro-1,1a,6,10b-tetrahydrodibenzo[a,e]cyclopropa[c]cyclohepten-6-one with hydroxylamine hydrochloride as described in Example 1A. The sodium salt was then reacted wit 2-dimethylaminoethylchloride hydrochloride as in Example 1B.

By the method described other nuclearly substituted 1,1a,6,10b-tetrahydrodibenzo[a,e]cyclopropa[c]cyclohepten-6-one oximes (Column 1 of Table I) react with 2-dimethylaminoethylchloride hydrochloride to yield the products in Column 2 of Table I.

TABLE I

| Example | Starting Oxime | Substituted Oxime |
|---|---|---|
| a. | 4-Bromo-1,1a,6,10b-tetrahydrodibenzo[a,e]cyclopropa[c] cyclohepten-6-one oxime | 4-Bromo-1,1a,6,10b-tetrahydrodibenzo[a,e]cyclopropa[c]cyclohepten-6-one O-[2-(dimethylamino)ethyl]oxime |
| b. | 4-Fluoro-1,1a,6,10b-tetrahydrodibenzo[a,e]cyclopropa[c]cyclohepten-6-one oxime | 4-Fluoro-1,1a,6,10b-tetrahydrodibenzo[a,e]cyclopropa[c]cyclohepten-6-one O-[2-(dimethylamino)ethyl]oxime |
| c. | 4-Trifluoromethyl-1,1a,6,10b-tetrahydrodibenzo[a,e]cyclopropa-[c]cyclohepten-6-one oxime | 4-Trifluoromethyl-1,1a,6-10b-tetrahydrodibenzo[a,e]cyclopropa[c]-cyclohepten-6-one O-[2-(dimethylamino)ethyl]oxime |
| d. | 4-Methyl-1,1a,6,10b-tetrahydro- | 4-Methyl-1,1a,6,10b-tetrahydrodi- |

TABLE I-continued

| Example | Starting Oxime | Substituted Oxime |
| --- | --- | --- |
| | dibenzo[a,e]cyclopropa[c]cyclo-hepten-6-one oxime | benzo[a,e]cyclopropa[c]cyclohepten-6-one 0-[2-(dimethylamino)ethyl]-oxime |
| e. | 4-Methylsulfonyl-1,1a,6,10b-tetrahydrodibenzo[a,e]cyclopropa[c]cyclohepten-6-one oxime | 4-Methylsulfonyl-1,1a,6,10b-tetrahydrodibenzo[a,e]cyclopropa[c]-cyclohepten-6-one 0-[2-(dimethyl-amino)ethyl]oxime |
| f. | 2-Chloro-1,1a,6,10b-tetrahydro-dibenzo[a,e]cyclopropa[c]cyclo-hepten-6-one oxime | 2-Chloro-1,1a,6,10b-tetrahydrodi-benzo[a,e]cyclopropa[c]cyclohepten-6-one 0-[2-(dimethylamino)ethyl]-oxime |
| g. | 4-N,N-Dimethylsulfonamido-1,1a,6,10b-tetrahydrodibenzo[a,e]-cyclopropa[c]cyclohepten-6-one oxime | 4-N,N-Dimethylsulfonamido-1,1a,6,10b-tetrahydrodibenzo[a,e]cyclo-propa[c]cyclohepten-6-one 0-[2-(dimethylamino)ethyl]oxime |
| h. | 4-Methylthio-1,1a,6,10b-tetra-hydrodibenzo[a,e]cyclopropa[c]-cyclohepten-6-one oxime | 4-Methylthio-1,1a,6,10b-tetra-hydrodibenzo[a,e]cyclopropa[c]-cyclohepten-6-one 0-[2-(dimethyl-amino)ethyl]oxime |
| i. | 4-n-Butoxy-1,1a,6,10b-tetra-hydrodibenzo[a,e]cyclopropa[c]-cyclohepten-6-one oxime | 4-n-Butoxy-1,1a,6,10b-tetrahydro-dibenzo[a,e]cyclopropa[c]cyclo-hepten-6-one 0-[2-(dimethylamino)-ethyl]oxime |

Dosage Forms

The antidepressant agents of this invention can be administered as treatment for psychiatric depression of the reactive and endogenous types by any means that produces contact of the active agent with the agent's site of action in the body of a mammal. In addition to their antidepressant activity they also have a beneficial sedative action. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 50 milligrams per kilogram of body weight. Ordinarily 0.05 to 40, and preferably 0.1 to 20 milligrams per kilogram per day given in divided doses 2 to 4 times a day or in sustained release form is effective to obtain desired results.

Dosage forms (compositions) suitable for internal administration contain from 2 milligrams to about 10 millgrams of active ingredient per unit. In these pharmaceutical compositions the active ingredient will ordinarily be present in an amount of about 0.01–90% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compresses tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage froms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA (ethylenediaminetetraacetic acid). In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences*, E. W. Martin, a standard reference text to this field.

Useful pharmaceutical dosage-forms for administration of the compounds of this invention can be illustrated as follows:

Capsules

Capsules can be prepared by filling standard two-piece hard gelatin capsules with the following mixture using conventional encapsulating equipment:

| | |
| --- | --- |
| Active ingredient | 5 mg. |
| Lactose | 125 mg. |
| Talc | 12 mg. |
| Magnesium stearate | 3 mg. |

Capsules

A mixture of active drug in soy bean oil is prepared and injected by means of a positive displacement pump in gelatin to form soft gelatin capsules containing 5 mg. of the active ingredient. The capsules are washed in petroleum ether and dried.

Tablets

Tablets can be prepared by conventional procedures so that each unit will contain:

| | | |
|---|---|---|
| Active ingredient | 5 | mg. |
| Spray dried lactose | 150 | mg. |
| Microcrystalline cellulose | 35 | mg. |
| Magnesium stearate | 3 | mg. |

Parenteral

Parenteral composition suitable for intra muscular administration is prepared so that each ml. contains:

| | | |
|---|---|---|
| Active ingredient | 5 | mg. |
| Sodium carboxy methyl cellulose | .75 | % |
| Polysorbate 80 | 0.04 | % |
| Benzyl alcohol | 0.9 | % |
| Sodium chloride | 0.9 | % |
| Water for injection Q.S. | 1 | ml. |

Suspension

An aqueous suspension is prepared for oral administration so that each 5 mls. contain:

| | | |
|---|---|---|
| Active ingredient | 5 | mg. |
| Methylcellulose | 5 | % |
| Carboxy methyl cellulose | 5 | % |
| Syrup | 30 | % |
| Polysorbate 80 | 0.2 | % |
| Sodium saccharin | 2 | mg. |
| Cherry flavor | 0.1 | % |
| Sodium benzoate | 5 | mg. |
| Water Q.S. | 5 | ml. |

Use

A standard procedure for detecting and comparing the antidepressant activity of compounds in this series for which there is good correlation with human efficacy is the prevention of tetrabenazine-induced sedation and depression in mice. (Everett, "The Dopa Response Potentiation Test and Its Use in Screening for Antidepressant Drugs" pp. 164–167 in "Antidepressant Drugs" [Proceedings of the First International Symposium], S. Garattini and M. N. G. Dukes, eds., 1967.).

Groups of 10 Carworth $CF_1S$ female mice, 18–21 g. each, were fasted 1.5 hours and were intubated with antagonist compounds at oral doses of 0, 5, 25, and 125 mg/kg or 0, 1, 3, 9, 27, and 81 mg/kg in 0.20 ml of 1% Methocel (methylcellulose). The mice were challenged 30 minutes later with tetrabenzine (as the methane-sulfonate), 32 mg/kg intraperitoneally (dissolved in 0.20 ml. 0.05M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse was lifted by the tail from a group of 10 in a testing box and placed on a stainless steel testing box lid (12.5 × 8 inches with 0.33 mesh) either turned its head horizontally 30° in both directions or moved to the edge of the screen within 10 seconds after being placed on the screen. Relief from ptosis was recorded when exactly 2 seconds after placing the mouse facing the observer, lid closure was less than 50% in both eyes. The following table gives results.

ANTAGONISM OF TETRABENAZINE-INDUCED
DEPRESSION IN MICE ORALLY AT 1 HOUR POST-DRUG

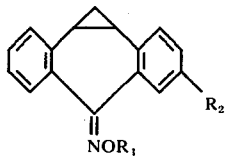

| COMPOUND | | $ED_{50}$ (mg/kg) FOR PREVENTION OF | |
|---|---|---|---|
| $R_2$ | $R_1$ | EXPLORATORY LOSS | PTOSIS |
| H | $-CH_2CH_2N(CH_3)_2$ | 2.3 | 0.4 |
| H | $-CH_2CH_2NH_2 \cdot HCl$ | 0.10 | 0.09 |
| H | $-CH_2CH_2CH_2N(CH_3)_2$ | 15.6 | 9.0 |
| H | $-CH_2CH_2NHCH_3$ | 1.9 | 0.33 |
| Cl | $-CH_2CH_2N(CH_3)_2$ | 11.2 | 7.2 |
| H | $-CH_2CH_2N(CH_3)_2 \cdot HCl$ | 1.4 | 0.5 |
| H | $-CH_2CH_2NH_2$ | 0.25 | 0.09 |
| H | $-CH_2CH_2N\!\!\left<\!\!\begin{array}{c}\text{pyrrolidine}\end{array}\!\!\right>$ | 10.4 | 4.8 |
| H | $-CH_2CH_2N\!\!\left<\!\!\begin{array}{c}\text{morpholine}\end{array}\!\!\right>\!O$ | 3.0 | 1.0 |
| H | $-CH_2CH_2N\!\!\left<\!\!\begin{array}{c}\text{piperidine}\end{array}\!\!\right>$ | 4.7 | 1.7 |
| H | $-CH_2CH_2N[CH(CH_3)_2]_2$ | 5.2 | 3.3 |

ANTAGONISM OF TETRABENAZINE-INDUCED
DEPRESSION IN MICE ORALLY AT 1 HOUR POST-DRUG -continued

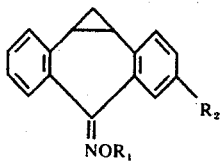

| COMPOUND | | $ED_{50}$ (mg/kg) FOR PREVENTION OF | |
|---|---|---|---|
| $R_2$ | $R_1$ | EXPLORATORY LOSS | PTOSIS |
| amitriptyline ("ELAVIL") | | 4.7 | 1.7 |
| imipramine ("TOFRANIL") | | 3.0 | 2.5 |
| 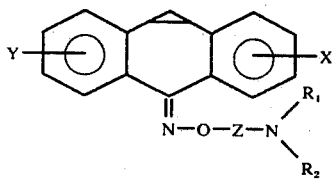 | | 6.5 | 3.2 |

I claim:

1. A pharmaceutical composition suitable for use as an antidepressant comprising a suitable pharmaceutical carrier and an effective antidepressant amount of a compound of the formula

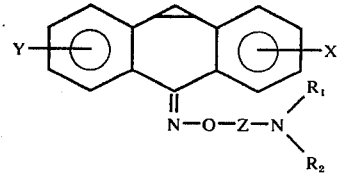

where
X or Y = H, F, Cl, Br, $C_1$–$C_4$ alkyl, $C_1$–$C_4$ alkoxy, $CF_3$, $CH_3S$, $CH_3SO_2$, $SO_2N(CH_3)_2$, provided that one is H;
Z = $C_2$–$C_3$ alkylene;
$R_1$ and $R_2$ independently = H or $C_1$–$C_4$ alkyl; and its pharmaceutically suitable salts.

2. The pharmaceutical composition of claim 1 where $R_1$ and $R_2$ = H or $CH_3$.

3. The pharmaceutical composition of claim 1 where X and Y = H, Z = ethylene, and $R_1$ and $R_2$ = H or $CH_3$; and its hydrochloride salt.

4. The pharmaceutical composition of claim 3 where $R_1$ and $R_2$ = H.

5. The pharmaceutical composition of claim 3 where $R_1$ = H and $R_2$ = $CH_3$.

6. The pharmaceutical composition of claim 3 where $R_1$ and $R_2$ = $CH_3$.

7. A method of alleviating depression in a mammal which comprises administering to the mammal an effective antidepressant amount of a compound of the formula:

where
X or Y = H, F, Cl, Br, $C_1$–$C_4$ alkyl, $C_1$–$C_4$ alkoxy, $CF_3$, $CH_3S$, $CH_3So_2$, $SO_2$ $N(CH_3)_2$, provided that one is H;
Z = $C_2$–$C_3$ alkylene;
$R_1$ and $R_2$ independently = H or $C_1$–$C_4$ alkyl; and its pharmaceutically suitable salts.

8. The method of claim 7 where $R_1$ and $R_2$ = H or $CH_3$.

9. The method of claim 7 where X and Y = H, Z = ethylene, and $R_1$ and $R_2$ = H or $CH_3$; and its hydrochloride salt.

10. The method of claim 9 where $R_1$ and $R_2$ = H.

11. The method of claim 9 where $R_1$ = H and $R_2$ = $CH_3$.

12. The method of claim 9 where $R_1$ and $R_2$ = $CH_3$.

* * * * *

UNITED STATES PATENT OFFICE
CERTIFICATE OF CORRECTION

PATENT NO. : 4,008,331

DATED : February 15, 1977

INVENTOR(S) : Roy Teruyuki Uyeda

It is certified that error appears in the above-identified patent and that said Letters Patent are hereby corrected as shown below:

In Claim 7, lines 38 and 39 of column 18, in place of

"$C_{1-C4}$ alkoxy, $CF_3$, $CH_3S$, $CH_3So_2$, $SO_2 \ N(CH_3)_2$,"

insert

-- $C_1-C_4$ alkoxy, $CF_3$, $CH_3S$, $CH_3SO_2$, $SO_2N(CH_3)_2$, --

Signed and Sealed this

Second Day of May 1978

[SEAL]

Attest:

RUTH C. MASON
Attesting Officer

LUTRELLE F. PARKER
Acting Commissioner of Patents and Trademarks